US005152456A

United States Patent [19]

Ross et al.

[11] Patent Number: 5,152,456

[45] Date of Patent: Oct. 6, 1992

[54] DISPENSING APPARATUS HAVING A PERFORATE OUTLET MEMBER AND A VIBRATING DEVICE

[75] Inventors: Calvin J. Ross, Suffolk; Victor C. Humberstone, Cambridge, both of United Kingdom

[73] Assignee: Bespak, PLC, King's Lynn, United Kingdom

[21] Appl. No.: 620,416

[22] Filed: Dec. 3, 1990

[30] Foreign Application Priority Data

Dec. 12, 1989 [GB] United Kingdom ................ 8928086
Aug. 10, 1990 [GB] United Kingdom ................ 9017563

[51] Int. Cl.⁵ ........................................ B05B 1/08
[52] U.S. Cl. .............................. 239/102.2; 239/4; 128/200.16; 261/DIG. 48
[58] Field of Search ............... 222/196; 239/4, 102.1, 239/102.2, 338, 101, 542; 128/200.16; 261/DIG. 48

[56] References Cited

U.S. PATENT DOCUMENTS

| | | | |
|---|---|---|---|
| 3,790,079 | 2/1974 | Berglund et al. | 239/4 X |
| 3,804,329 | 4/1974 | Martner . | |
| 3,812,854 | 5/1974 | Michaels et al. . | |
| 4,261,512 | 4/1981 | Zierenberg | 239/4 X |
| 4,294,407 | 10/1981 | Reichl et al. | 239/102.2 |
| 4,368,476 | 1/1983 | Uehara et al. . | |
| 4,479,609 | 10/1984 | Maeda et al. | 239/102.2 |
| 4,530,464 | 7/1985 | Yamamoto et al. . | |
| 4,533,082 | 8/1985 | Maehara et al. . | |
| 4,605,167 | 8/1986 | Maehara . | |
| 4,702,418 | 10/1987 | Carter et al. . | |
| 4,790,479 | 12/1988 | Matsumoto et al. | 239/102.2 |
| 4,888,516 | 12/1989 | Daeges et al. | 239/102.2 X |
| 5,021,701 | 6/1991 | Takahashi et al. | 239/102.2 X |

FOREIGN PATENT DOCUMENTS

| | | | |
|---|---|---|---|
| 105608 | 7/1982 | Japan | 239/102.2 |
| 62411 | 4/1983 | Japan | 239/102.2 |
| 4714 | 1/1985 | Japan | 239/102.2 |
| 1454597 | 11/1976 | United Kingdom . | |
| 2177623 | 1/1987 | United Kingdom . | |

OTHER PUBLICATIONS

Review of Scientific Instruments, vol. 57, No. 11, Nov. 1986, pp. 2870-2876, American Institute of Physics; New York, US; N. Maehara et al.: "Influence of the Vibrating System of a Multipinhole-Plate Ulyrasonic Nebulizer . . . ".

*Primary Examiner*—Kevin P. Shaver
*Assistant Examiner*—Kenneth DeRosa
*Attorney, Agent, or Firm*—Beveridge, DeGrandi & Weilacher

[57] ABSTRACT

Dispensing apparatus (1) comprises a housing (2) defining a chamber (3) receiving liquid (4) to be dispensed and comprising a perforate membrane which defines a front wall of the chamber. A vibrating device (8) is connected to the housing and is operable to vibrate the perforate membrane to dispense droplets of liquid through holes (25) in the perforate membrane. The housing comprises an annular member (11) having a relatively thin inner annular portion (68) connected to the perforate membrane and a relatively thick outer annular portion (66) connected to the vibrating device. The apparatus is suitable for dispensing pharmaceutical products as an atomized mist and provides a hand-held inhaler for oral inhalation.

17 Claims, 4 Drawing Sheets

DISPENSING APPARATUS HAVING A PERFORATE OUTLET MEMBER AND A VIBRATING DEVICE

This invention relates to dispensing apparatus for use in dispensing liquid as an atomized spray and in particular but not exclusively to medical atomizers.

It is known to produce a stream of liquid droplets by vibrating a perforate membrane having a rear face contacted by liquid such that droplets are expelled from holes in the membrane at each cycle of vibration. The size of droplet produced will depend upon the hole size and for practical purposes the thickness of the membrane will tend to be of the same order of magnitude as the hole size. Consequently it has hitherto not been practicable to use such apparatus for the production of an atomized and spray for use in applications such as medical inhalers where for example droplet size of less than 10 microns may be required.

It is known from U.S. Pat. No. 4,533,082 to provide dispensing apparatus comprising a housing defining a chamber receiving in use a quantity of liquid to be dispensed, the housing comprising a perforate member which defines a front wall of the chamber and which has a rear face contacted by liquid in use, the apparatus further comprising vibrating means connected to the housing and operable to vibrate the perforate membrane to dispense droplets of liquid through the perforate membrane.

The present invention is characterized in that the housing comprises an annular member having a relatively thin inner annular portion connected to the perforate membrane and a relatively thick outer annular portion connected to the vibrating means.

An advantage of this arrangement is that the vibrating means is presented with a relatively high acoustic impedance compared with a relatively low impedance found in the inner annular portion so that the amplitude of vibration transmitted to the perforate member is amplified during transmission of transverse acoustic waves through the annular member.

An efficient arrangement is thereby attainable when vibrating the perforate membrane at the higher frequencies favored for the production of smaller droplets.

Preferably the annular member comprises a disc defining a central aperture bounded by the inner annular portion and traversed by the perforate membrane and wherein the thickness of the disc tapers in a radially inward direction.

Such a disc may be regarded as an impedance transformer in which the outer annular portion is matched in impedance to a vibrating means such as a piezoelectric transducer and the inner annular portion is matched in impedance to the perforate membrane.

Advantageously the disc has front and rear faces which converge at an angle of taper which varies with radius such that the inner annular portion has a smaller angle of taper than that of the outer annular portion.

The perforate membrane may comprise a sheet defining an array of holes through which liquid is dispensed in use and may include support means supporting the sheet comprising a grid of support elements.

Such support means has the advantage of providing stiffness to sheets which may be formed of very thin material in order to facilitate the provision of correspondingly small hole diameters. A further surprising advantage is that the proportion of holes which dispense droplets is enhanced by the presence of support elements and those holes in close proximity with a support element are found to be more likely to dispense droplets than would otherwise be the case.

Conveniently the support elements are formed integrally with the sheet and comprise thickened portions thereof.

Preferably the support means comprises a plurality of circumferentially spaced radially extending elements connected to an annular support element defining a central portion of the sheet.

Such an arrangement is believed to operate more effectively than support means in which the radially extending elements meet at a central location of the sheet. The central portion of the sheet defined by the annular support element is found to operate efficiently in the production of droplets.

Preferably at least a front face of the perforate membrane comprises a liquid repellant surface. A suitable surface coating may conveniently be applied to the membrane to render the surface liquid repellant.

Efficient dispensing operation requires that the front face of the membrane should not be wetted by the liquid. The use of a liquid repellant surface coating inhibits such wetting and thereby improves efficiency.

Conveniently the vibrating means comprises a transducer removably connected to the housing whereby in use a housing from which liquid has been dispensed can be replaced by a further housing charged with liquid.

Advantageously the perforate membrane defines an array of holes each provided with a flared mouth formed in the rear face of the membrane whereby the hole tapers in cross-section in a direction towards a front face of the membrane.

The presence of the taper facilitates the flow of liquid particularly where the liquid to be dispensed contains a particulate substance in suspension. The presence of the taper is believed to prevent clogging of the holes by accummulation of particulate material.

Preferably the perforate membrane comprises an electroformed metal sheet. Such sheets may be manufactured to any desired thickness and the size and shape of holes can be controlled using a photographic process. A result of such a process is the formation of tapered holes on one side of the sheet which has the particular advantage referred to above.

Preferred embodiments of the present invention will now be described by way of example only and with reference to the accompanying drawings of which:

Figure 1:
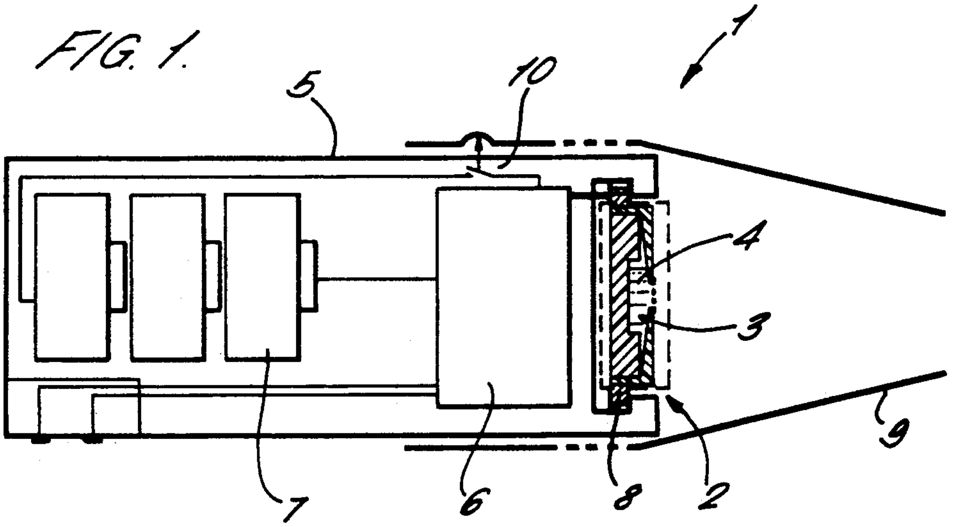
FIG. 1 is a schematic section of a hand held dispensing apparatus.

FIG. 1 shows dispensing apparatus 1 which is a hand held inhaler for medical use. Apparatus 1 comprises a housing 2 defining a chamber 3 containing liquid 4 to be dispensed.

The housing 2 is mounted on a hand held casing 5 within which is located an electronic control circuit 6 and batteries 7. An electro acoustic transducer 8 of the piezoelectric type is mounted on the housing 2 and is powered and controlled by the control circuit 6. A mouthpiece 9 fits slidably on the casing 5 and movement of the mouthpiece 9 relative to the casing actuates an on-off switch 10.

Figure 3:
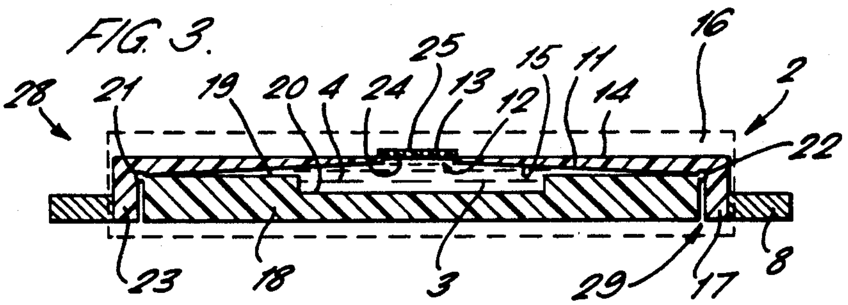
FIG. 3 is a sectional elevation of the spray head of the apparatus of FIGS. 1 and 2.

The detailed construction of the housing 2 and transducer 8 can be seen from FIG. 3. The housing comprises a disc 11 having a central aperture 12 with a thin perforate membrane 13 bonded to the disc so as to overlay the aperture. The construction of a suitable membrane 13 is described below with reference to FIGS. 8 and 9. The membrane 13 is perforated by a large number of holes 25 of which only a few are included in FIG. 3 by way of schematic representation. The disc 11 has a flat front face 14 and a frusto-conical rear face 15 so that the disc tapers linearly in thickness in the radially inward direction towards the perforate membrane 13.

The disc 11 has a periphery 16 from which projects rearwardly a tubular portion 17.

The housing 2 also includes a circular base 18 which fits within the tubular portion 17 so that a chamber 3 is defined between the base and the disc 11. The base 18 has a front face 19 having a central recess 20 such that the chamber 3 is deepest in the region adjacent to the membrane 13.

An annular rib 21 is formed on the base 18 peripherally of the front face 19 and locates in an annular groove 22 formed in the disc 11 thereby sealing the chamber 3. An annular space 29 is formed between the tubular portion 17 and the base 18.

The transducer 8 is a circular ring piezoelectric element and is bonded to a rearward end 23 of the tubular portion 17.

The transducer 8 is arranged such that when energized and with an alternating voltage the transducer expands and contracts radially to impart an ultrasonic vibration to the tubular portion 17. The thickness of the rearward end 23 (measured in the direction in which it is vibrated by the transducer) is considerably thicker than the thickness of the disc 11 at the point of contact with the membrane 13. The disc 11 flexes in response to radially outward movement of the transducer by pivotal action about the annular rib 21 so as to move the membrane 13 axially towards the base 18. On radial contraction of the transducer 8 pivotal action about the rib 21 causes flexure of the disc so as to move the membrane 13 away from the base 18. At ultrasonic frequencies however the movement of the disc 11 can be characterised more in terms of transmission of transverse acoustic wave motion in a direction radially inward through the disc 11. The effect of the taper present in the shape of the disc 11 results in the amplitude of such transverse vibrations increasing progressively in the radially inward direction to thereby maximize the axial displacement of the membrane 13. The increase in amplitude is associated with the decreasing impedance of the disc 11 in the radially inward direction.

In use to dispense liquid, the apparatus 1 is held in an orientation in which liquid 4 is in contact with the rear surface 24 of the perforate membrane 13. Prior to actuation of the transducer 8 there will generally be no loss of liquid through the holes 25 in the membrane 13 since a liquid surface formed in the holes will generally have sufficient surface tension to resist the outflow of liquid. Dispensing operation is commenced by the user actuating the switch 10 so that the transducer 8 is energised to vibrate at ultrasonic frequency. This vibration is conducted by the disc 11 to the perforate membrane 13. During rearward motion of the vibrating membrane 13 an instantaneous pressure rise in the liquid adjacent to the membrane will result in the surface tension being overcome and droplets of liquid being ejected through the holes 25.

A fine mist of atomized liquid is dispensed through the membrane 13 into the mouthpiece 9 and is inhaled by the user.

The apparatus 1 is shown in its normal orientation for oral dispensing in which the membrane 13 is approximately vertical.

Continued operation will deplete the quantity of liquid within the chamber 4 so that eventually dispensing will no longer be possible once there is no liquid in contact with the rear surface 24 of the membrane 13. The recess 20 in the base 18 ensures that the bulk of the liquid is stored adjacent to the membrane 13 to thereby minimize the amount of liquid wastage which occurs when there is insufficient liquid remaining in the chamber 3 for dispensing operation to continue.

Figure 2:
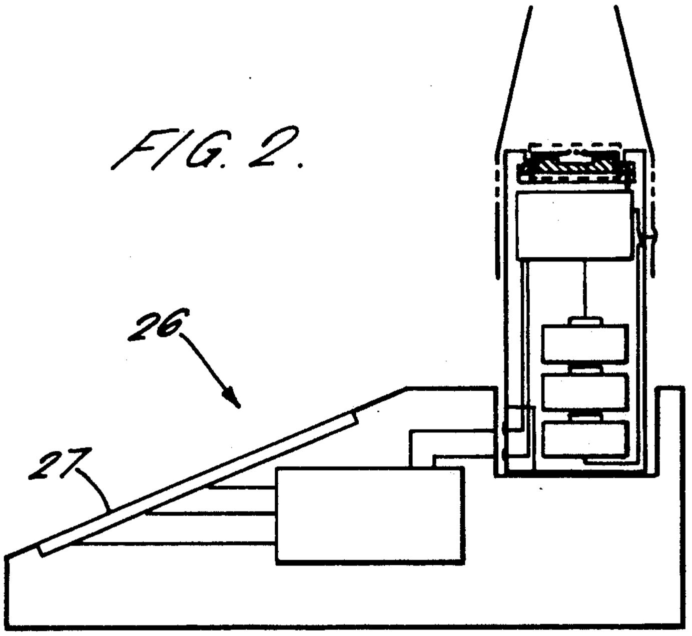
FIG. 2 is a schematic section of the apparatus of FIG. 1 connected to an electronic control unit.

The apparatus 1 may be programmed to deliver a predetermined dose of atomized and liquid by means of a timer within the control circuit 6 which allows the transducer 8 to be energized for a predetermined time period. The control circuit 6 may be programmed by means of an electronic control unit 26 as shown schematically in FIG. 2, the control unit having a keyboard 27 for the input of data.

Once the supply of liquid 4 is exhausted or depleted to the extent of being unusable a replacement housing 2 can be fitted to the casing 5 and containing a new supply of liquid.

The housing 2 is arranged to be received as a sliding fit within the transducer 8 for ease of replacement.

Figure 4:
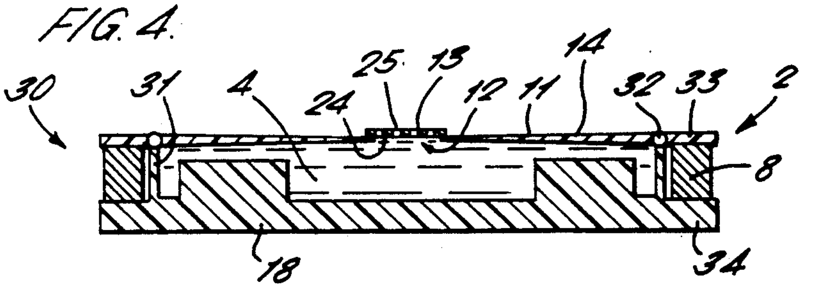
FIGS. 4, 5, 6 and 7 are sectional elevations of further alternative spray heads.

The housing 2 and the transducer 8 together comprise a spray head 28. An alternative spray head 30 as shown in FIG. 4 will now be described. Corresponding reference numerals to those of preceding figures are used where appropriate for corresponding elements.

The alternative spray head 30 has a base 18 including an annular flange 31 constituting a side wall of the chamber 4. The flange 31 has a lip 32 to which the disc 11 is bonded such that a peripheral portion 33 of the disc projects radially outward from the flange 31.

The base 18 of the alternative spray head 30 includes a radially projecting portion 34 and a piezoelectric transducer 8 is located outboard of the flange 31 in contact with the peripheral portion 33 of the disc 11 and the radially projecting portion 34 of the base 18. The transducer 8 is of a type producing axial expansion and contraction when energized such that when actuated by the control circuit 6 it produces an ultrasonic vibration of the peripheral portion 33.

This vibration is communicated by pivotal action about the lip 32 to the perforate membrane 13. Ultrasonic transverse waves transmitted radially inwardly through the disc 11 are amplified by virtue of a linear taper of the disc 11.

Liquid 4 in contact with the rear surface of the membrane 13 is dispensed through holes 25 as a fine atomized mist.

Figure 5:
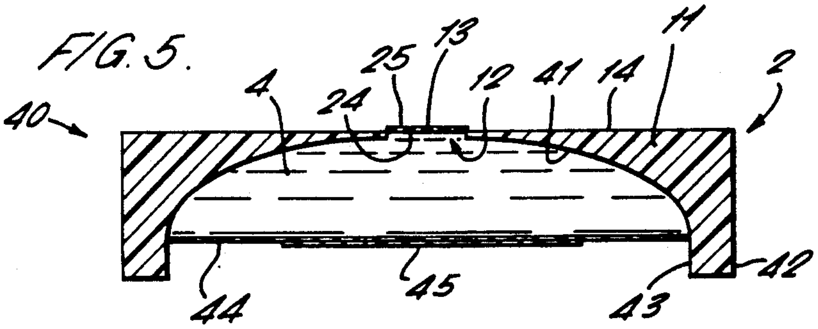

A further alternative spray head 40 is shown in FIG. 5 and will be described using reference numerals corresponding to those of previous figures where appropriate for corresponding elements.

The spray head 40 includes a disc 11 having a planar front face 14 and a dished rear face 41. The rear face 41 is profiled such that the thickness of the disc 11 tapers radially inwardly in an approximately exponential manner. The disc 11 includes a rearwardly extending tubular portion 42 having an internal surface 43 which merges smoothly with the rear surface 41. A plate 44 is located within the tubular portion 42 so as to constitute a rear wall of the chamber 4. A piezoelectric disc transducer 45 is bonded centrally to the plate 44 and is of a type which expands and contracts radially when energized.

In use the transducer 45 is energized so as to vibrate radially at ultrasonic frequencies and this vibration is communicated through the plate 44 to the tubular portion 42. Transverse wave motion is propagated through the tubular portion in an axial direction and is conducted along a curved path following approximately the curvature of the rear surface 41 to vibrate the perforate membrane 13. The amplitude of this vibration is progressively amplified by virtue of the tapered thickness of the disc 11.

The plate 44 and transducer 45 are renewable together with the disc 14 when a fresh housing 2 is fitted into an apparatus 1 with a fresh supply of liquid 4.

Figure 6:
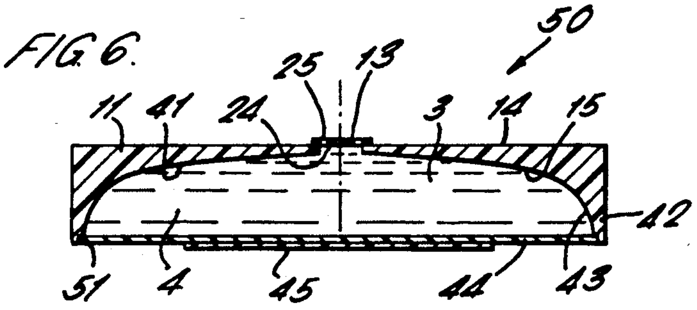

A further alternative spray head 50 is shown in FIG. 6 and is described with corresponding reference numerals to those of FIG. 5 for corresponding elements where appropriate.

The spray head 50 includes a disc 11 having a dished rear face 41 and a tubular portion 42. An internal surface 43 of the tubular portion 42 is stepped to provide a shoulder 51 against which a plate 44 is located and bonded. The plate 44 supports a central disc transducer 45 arranged to radially vibrate the membrane.

The spray head 50 differs from the spray head 40 of FIG. 5 in that the tubular portion 42 is thinner in radial width than the corresponding tubular portion of FIG. 5 and provides a shoulder 51 for positively locating the plate 44.

The thickness of the membrane 13 in the above apparatus can be typically in the range 1 to 80 microns. The size of holes 25 can be typically of the range 1 to 200 microns depending on the required droplet size. The apparatus is however particularly useful in applications where small droplets are required such that the thickness of the membrane 13 and the size of the holes 25 are less than 20 microns. The membrane 13 may be provided with holes 25 of uniform or non-uniform hole size depending on the required distribution of droplet size.

Figure 7:
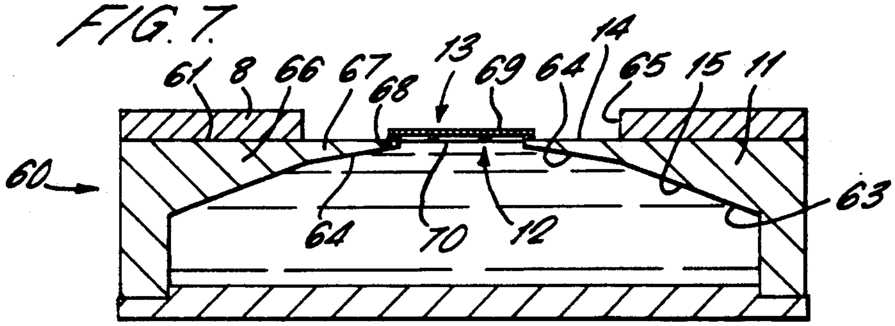

A further alternative spray head 60 is shown in FIG. 7 where corresponding reference numerals to those of previous figures are used where appropriate for corresponding elements.

The spray head 60 has a disc 11 formed of aluminium alloy and having a circular planar front face 14 of 22 mm diameter. An annular piezoelectric transducer 8 having an internal radius of 10 mm is bonded to a peripheral portion 61 of the front face 14 so as to be radially spaced from a circular central aperture 12 of the disc 11 having a diameter of 4 mm.

The disc 11 tapers in thickness in the radially inward direction such that a rear face 15 of the disc 11 has an outer annular portion 62 which tapers at an angle of 20° relative to the front face 14 when viewed in radial section and an inner annular portion 63 which tapers at an angle of 10° relative to the planar front face 14. The inner annular portion 63 joins the outer annular portion 62 at a circular interface 64 which is adjacent the radially inner edge 65 of the transducer 8. The transducer 8 thereby is bonded to a relatively thick outer portion 66. A relatively slender inner portion 67 of the disc 11 defines the aperture 12.

Figure 8:
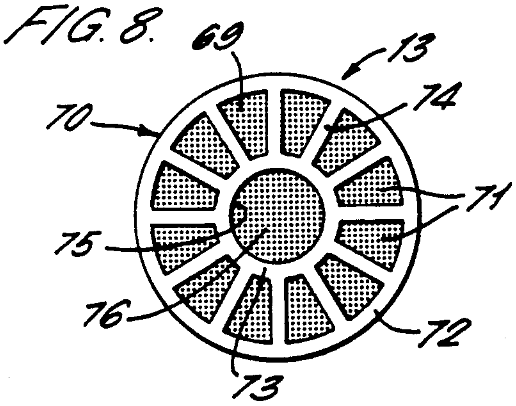
FIG. 8 is a view of the rear face of a perforate membrane for use in a spray head of any of the preceding figures.

A perforate membrane 13 overlays the aperture 12 and is bonded to an edge portion 68 of the inner portion 67. The perforate membrane 13 as shown in FIGS. 8 and 9 comprises a nickel sheet 69 having an integrally formed support 70 in the shape of a grid having circular symmetry as shown in FIG. 8.

The support 70 comprises thickened elements 72, 73 and 74 of the membrane 13 defining a series of apertures 71 which expose corresponding portions of the sheet 69. The support 70 has an outer annular element 72 which is connected to an inner annular element 73 by radial elements 74 defining the apertures 71 therebetween. A central aperture 75 is defined within the inner annular element 73 thereby exposing a central portion 76 of the sheet 69. The membrane 13 is formed in an electroforming process in which nickel is electro-deposited on selected areas of a substrate masked using a photographic process and the resulting sheet 69 is then detached from the substrate. The outer annular element 72 of the support 70 is bonded to the edge portion 68 so that vibration of the disc is conducted through the support to the sheet 69.

The membrane 13 is coated in a liquid repellant coating 80 using a commercially available surface treatment process in which sub-micron particles of polytetrafluroethylene are incorporated in a nickel phosphorous matrix which is auto-catalytically applied to the nickel material of the sheet 69 and support 70. A small proportion of phosphorous co-deposited with the nickel enhances the corrosion resistance of the resulting finish.

Figure 9:
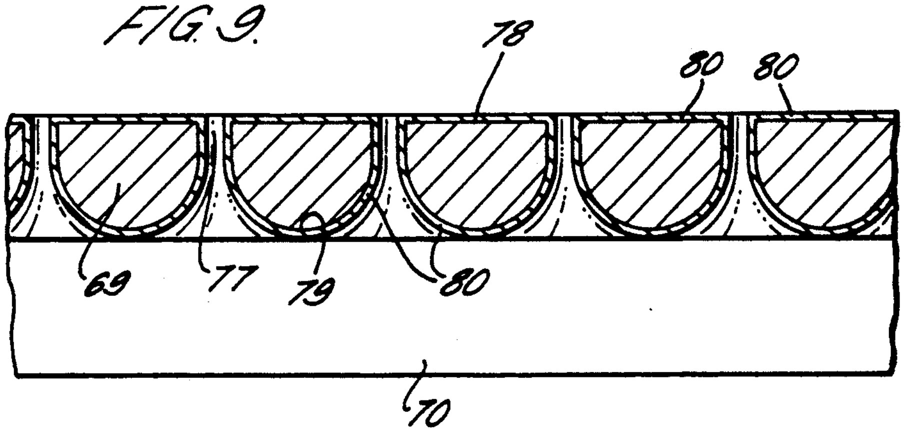
FIG. 9 is a sectioned elevation of a perforate sheet portion of the perforate membrane of FIG. 8.
Figure 10:
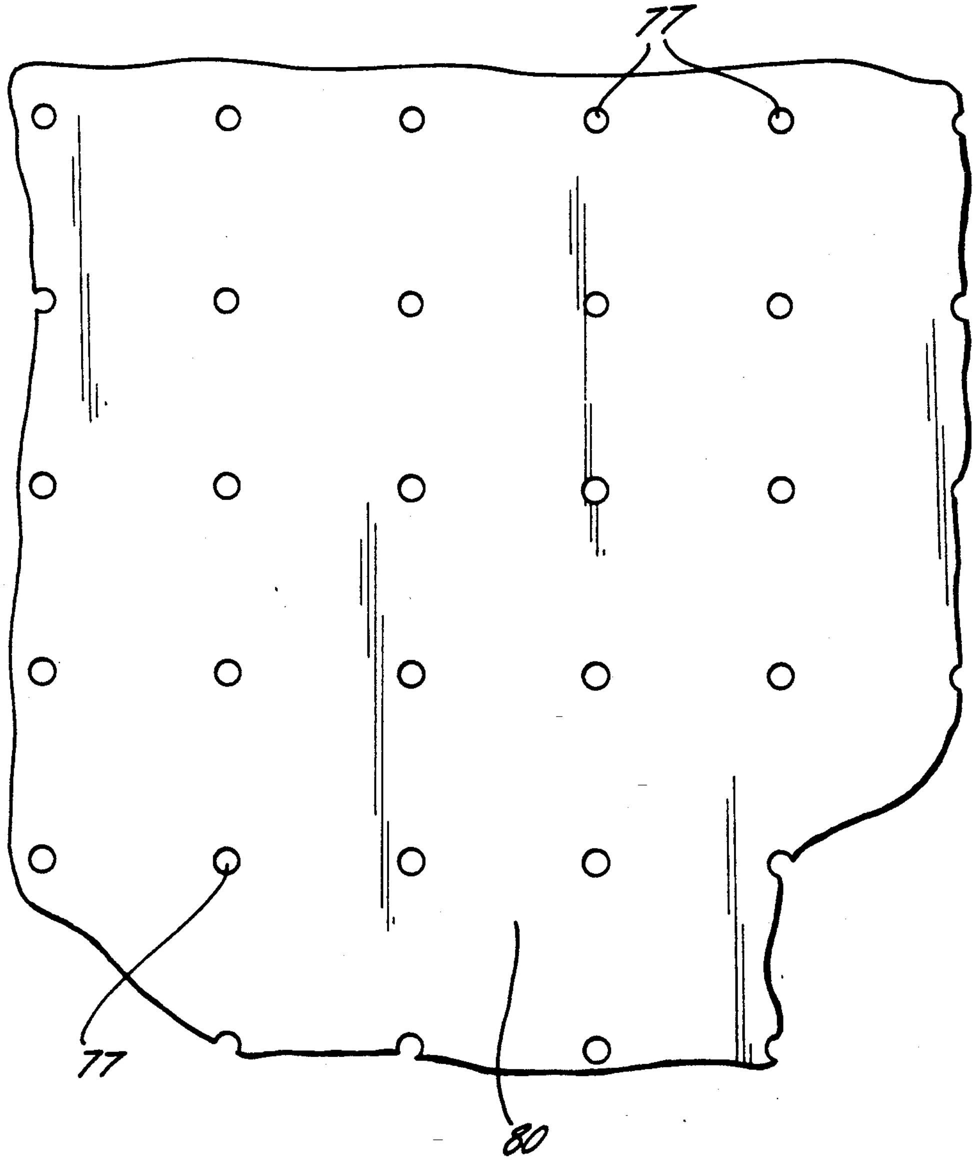
FIG. 10 is a plan view of a perforate sheet portion of the perforate membrane of FIG. 8.

As shown in FIGS. 9 and 10 the sheet 69 includes a regular array of circular holes 77 and has a front face 78 to which the support 70 is bonded. The sheet 69 has a rear face 79 which is normally contacted by liquid 4 and the holes 77 are flared such that the cross-section of each hole narrows in a direction from the rear face 79 towards the front face 78.

The resulting holes 77 in the sheet 69 are of 3 microns diameter and 25 microns spacing. The resulting droplets are formed in the range 5 to 7 microns when dispensing a pharmaceutical product in aqueous solution, this droplet size being suitable for delivery of atomized products to the lungs of a patient. A typical flow rate in the range 10 to 20 cubic millimeters per second is achieved, the flow rate being dependent on the power and frequency with which the transducer 8 is driven.

The sheet 69 includes approximately 1500 holes 77 of which only a proportion will emit droplets in use. Those of the holes 77 which do emit droplets tend to be concentrated in regions adjacent to the thickened elements 72, 73 and 74 and also in the central portion 76. The number of such holes 77 which do emit droplets will also depend on the amplitude of vibration induced in the membrane 13 and in a typical example the proportion of holes which emit droplets is about 10%.

The size of the droplets produced is closely dependent on the diameter of the holes 77 so that for different applications it may be necessary to use a sheet having different hole size.

Apparatus in accordance with the present invention may be used to dispense products in solution or suspension. Pharmaceutical products will generally require the presence of a preservative in aqueous solution such as benzalkonium chloride which has a tendency to reduce the surface tension of the resulting solution. When dispensing such solutions it is particularly important for the sheet 69 to be treated with a liquid repellant coating and for the external surface of the sheet to be as smooth as possible in order to reduce the tendency of the solution to wet the external surface of the sheet. Alternative liquid repellant coatings may be used such as silanes, fluorosilanes, micronised PTFE (polytetrafluoroethylene) particles and PTFE applied and heated in situ to form a conformal coating.

The control circuit 6 includes a simple oscillator circuit arranged to drive the transducer 8 at a frequency typically in the range of 3 KHz to 1 MHz selected to be at resonant frequency of the transducer in order to maximize efficiency. The resonant frequency of the transducer 8 is matched to that of the disc 11 so as to achieve maximum amplitude of vibration at the membrane 13.

The chamber 3 containing liquid 4 is a closed chamber which would not normally have any means of inducing excess pressure within the chamber. The emission of atomized spray droplets through the membrane 13 is achieved in the above embodiments solely by vibration of the membrane and not by supplying excess pressure to the liquid by other means.

The vibration of the membrane 13 achieved by the apparatus of the present invention does not rely on the transmission through the liquid 4 of ultrasonic waves so that problems associated with cavitation in the liquid are avoided.

The apparatus will function in any orientation provided the level of liquid 4 in the chamber 3 is such that liquid is maintained in contact with the rear surface 79 of the perforate membrane 13.

The apparatus may optionally be provided with a sensor responsive to inhalation by the user through the mouthpiece. The control circuit may then be programmed to dispense only after commencement of inhalation has been sensed.

Control circuitry for the apparatus may include a memory and microprocessor to monitor the accumulative dispensed volume and control the duration of delivery and the time interval between successive deliveries. The apparatus may also optionally be provided with visual or audible indicators to provide indication of for example elapsed time since last use, warning that the remaining liquid is nearly depleted and indication that the next dispensing cycle is due.

The membrane may alternatively be provided with holes which are other than circular. The membrane may alternatively comprise a perforate sheet without having a support. Where a membrane is provided with a support, the support may be other than of circular symmetry and may for example be in the form of a rectangular grid.

We claim:

1. Dispensing apparatus comprising a housing defining a chamber receiving in use a quantity of liquid to be dispensed, the housing comprising a perforate membrane which defines a front wall of the chamber, the membrane having a rear face contacted by the liquid in use, the apparatus further comprising vibrating means connected to the housing and operable to vibrate the perforate membrane by means of vibrations conducted through the housing to dispense droplets of the liquid through the perforate membrane, wherein the housing comprises an annular member having a relatively thin inner annular portion connected to the perforate membrane and a relatively thick outer annular portion connected to the vibrating means, the annular member comprising a disc defining a central aperture bounded by the inner annular portion and traversed by the perforate membrane, and wherein the thickness of the disc tapers in a radially inward direction.

2. Dispensing apparatus as claimed in claim 1 wherein the disc has front and rear faces which converge at an angle of taper which varies with radius such that the inner annular portion has a smaller angle of taper than that of the outer annular portion.

3. Dispensing apparatus as claimed in claim 1 wherein at least a front face of the perforate membrane comprises a liquid repellant surface.

4. Dispensing apparatus as claimed in claim 1 wherein the vibrating means comprises a transducer removably connected to the housing and whereby in use the housing from which liquid has been dispensed can be replaced by a further housing charged with liquid.

5. Dispensing apparatus as claimed in claim 1 wherein the perforate membrane defines an array of holes each provided with a flared mouth formed in the rear face of the membrane whereby the hole tapers in cross-section in a direction towards a front face of the membrane.

6. Dispensing apparatus as claimed in claim 1 wherein the perforate membrane comprises an electroformed metal sheet.

7. Dispensing apparatus as claimed in claim 1 wherein the perforate membrane comprises a sheet defining an array of holes through which liquid is dispensed in use and support means supporting the sheet comprising a grid of support elements.

8. Dispensing apparatus as claimed in claim 7 wherein the support elements are formed integrally with the sheet and comprise thickened portions thereof.

9. Dispensing apparatus as claimed in claim 7 wherein the grid of support elements comprises a plurality of circumferentially spaced radially extending elements connected to an annular support element defining a central portion of the sheet.

10. Dispensing apparatus comprising a housing defining a chamber receiving in use a quantity of liquid to be dispensed, the housing comprising a perforate membrane which defines a front wall of the chamber and which has a rear face contacted by liquid in use, the apparatus further comprising vibrating means connected to the housing and operable to vibrate the perforate membrane to dispense droplets of liquid through the perforate membrane, wherein the perforate membrane comprises a sheet defining an array of holes through which liquid is dispensed in use and support means supporting the sheet comprising a grid of support elements.

11. Dispensing apparatus as claimed in claim 10 wherein the support elements are formed integrally with the sheet and comprise thickened portions thereof.

12. Dispensing apparatus as claimed in claim 10 wherein the grid of support elements comprises a plurality of circumferentially spaced radially extending elements connected to an annular support element defining a central portion of the sheet.

13. Dispensing apparatus comprising a housing defining a chamber receiving in use a quantity of liquid to be dispensed, the housing comprising a perforate membrane which defines a front wall of the chamber and which has a rear face contacted by liquid in use, the apparatus further comprising vibrating means connected to the housing and operable to vibrate the perforate membrane to dispense droplets of liquid through the perforate membrane, the housing comprising an annular member having a relatively thin inner annular portion connected to the perforate membrane and a relatively thick outer annular portion connected to the vibrating means, wherein the perforate membrane comprises a sheet defining an array of holes through which liquid is dispensed in use and support means supporting the sheet comprising a grid of support elements.

14. Dispensing apparatus as claimed in claim 13, wherein the support elements are formed integrally with the sheet and comprise thickened portions thereof.

15. Dispensing apparatus as claimed in claim 13, wherein the grid of support elements comprises a plurality of circumferentially spaced radially extending elements connected to an annular support element defining a central portion of the sheet.

16. Dispensing apparatus comprising a housing defining a chamber receiving in use a quantity of liquid to be dispensed, the housing comprising a perforate membrane which defines a front wall of the chamber and which has a rear face contacted by liquid in use, the apparatus further comprising vibrating means connected to the housing and operable to vibrate the perforate membrane to dispense droplets of liquid through the perforate membrane, the housing comprising an annular member having a relatively thin inner annular portion connected to the perforate membrane and a relatively thick outer annular portion connected to the vibrating means, wherein the perforate membrane defines an array of holes each provided with a flared mouth formed in the rear face of the membrane whereby the hole tapers in cross-section in a direction towards a front face of the membrane.

17. A method of dispensing liquid as an atomized spray comprising the steps of containing a quantity of liquid in a chamber defined by a housing, said housing comprising a perforate membrane defining a front wall of the chamber whereby the membrane has a rear face contacted by the liquid, and operating a vibrating means connected to the housing to produce vibrations conducted through the housing to the perforate membrane whereby droplets of the liquid are dispensed through the perforate membrane, the method including the step of amplifying the amplitude of vibrations conducted to the perforate membrane by means of the housing comprising a disc defining a central aperture bounded by an inner annular portion connected to the perforate membrane, said disc tapering in thickness in a radially inward direction such that vibrations conducted in said radially inward direction from the vibrating means to the perforate membrane are amplified.

* * * * *